US008486468B2

(12) United States Patent
Asger et al.

(10) Patent No.: US 8,486,468 B2
(45) Date of Patent: Jul. 16, 2013

(54) PORPHYRIN CONTAINING LACTIC ACID BACTERIAL CELLS AND USE THEREOF

(75) Inventors: Geppel Asger, Gentofte (DK); Børge Windel Kringelum, Ballerup (DK); Ken Flemming Hansen, Birkerod (DK); Stig Lykke Iversen, Copenhagen O (DK); Claus Maxel Henriksen, Copenhagen O (DK)

(73) Assignee: Chr. Hansen A/S, Horsholm (DK)

( * ) Notice: Subject to any disclaimer, the term of this patent is extended or adjusted under 35 U.S.C. 154(b) by 248 days.

(21) Appl. No.: 11/979,166

(22) Filed: Oct. 31, 2007

(65) Prior Publication Data

US 2008/0057156 A1    Mar. 6, 2008

Related U.S. Application Data

(60) Division of application No. 09/767,680, filed on Jan. 24, 2001, now abandoned, which is a continuation-in-part of application No. 09/488,644, filed on Jan. 21, 2000, now abandoned, and a continuation of application No. PCT/DK01/00036, filed on Jan. 18, 2001.

(51) Int. Cl.
A23C 9/127    (2006.01)

(52) U.S. Cl.
USPC .................. 426/15; 426/19; 426/34; 426/36; 426/49; 426/54; 435/139; 435/161; 435/147; 435/150; 435/158

(58) Field of Classification Search
USPC .... 426/15, 19, 34, 36, 49, 54, 55, 7; 435/139, 435/147, 150, 158, 161, 41, 71.3
See application file for complete search history.

(56) References Cited

U.S. PATENT DOCUMENTS

| 4,588,595 | A | * | 5/1986 | Okonogi et al. ............ 435/252.4 |
| 5,075,226 | A | * | 12/1991 | Kaneko et al. ................ 435/148 |
| 5,527,505 | A | * | 6/1996 | Yamauchi et al. ............... 420/42 |
| 5,702,923 | A | * | 12/1997 | Vandenbergh et al. ...... 435/71.3 |
| 2001/0033878 | A1 | | 10/2001 | Geppel et al. |
| 2005/0032196 | A1 | | 2/2005 | Duwat et al. |

FOREIGN PATENT DOCUMENTS

| DK | EP 0 937 774 | * | 8/1999 |
| EP | 0430406 | | 6/1991 |
| JP | 04036180 | | 2/1992 |
| WO | WO 00/05342 | | 2/2000 |
| WO | WO 01/52668 | | 7/2001 |

OTHER PUBLICATIONS

Kaneko, T. et al. 1990. Acetoin fermentation by citratre positive Lactococcus lactis subsp. lactis 3022 grown aerobically in the presence of hemin of Cu. Appl. Environ. Microbiol. 56: 2644-2649.*

(Continued)

Primary Examiner — D. Lawrence Tarazano
Assistant Examiner — Hamid R Badr
(74) Attorney, Agent, or Firm — Hunton & Williams LLP

(57) ABSTRACT

Culturally modified lactic acid bacterial cells containing a porphyrin compound and their use in a novel method of reducing the oxygen content in a food and feed product or starting material is provided and means of improving the shelf life and/or quality of such products by using the culturally modified bacterial cells. Such culturally modified cells are useful in the manufacturing of a food and a feed product and for the manufacturing of metabolites produced by modified cells.

8 Claims, 13 Drawing Sheets

OTHER PUBLICATIONS

Ritchey, T. W. et al. 1976. Distribution of cytochrome-like respiration in Streptococci. J. Gen. Microbiol. 93: 195-203.*

Bolotin, Alexander et al., Low-Redundancy Sequencing of the Entire *Lactococcus lactis* IL1403 Genome, Antonie van Leeuwenhoek 76:27-76 (1999).

Chen, Wilfred et al., Intracellular Expression of Vitreoscilla Hemoglobin Alters the Aerobic Metabolism of Saccharomyces Cervisiae, Biotechnology Progress, May/Jun. 1994, 10:308-313.

Frustaci, Jana M. et al., The *Eschericia coli visA* Gene Encodes Ferrochelatase, the Final Enzyme of the Heme Biosynthetic Pathway, Journal of Bacteriology, Apr. 1993, p. 2154-2156.

Gil, Alicia et al., The Cytochrome Composition of the Meat Spoilage Bacterium *Brochothix themosphacta*: identification of cytochrome $a_3$- and $d$-type terminal oxidases under various conditions, Arch Microbial, 1992, 158:226-233.

Hackett, Neil R . et al., Membrane Cytochromes of *Escherichia coli* Grown Aerobically and Anaerobically with Nitrate, Journal of Bacteriology, May 1983, p. 708-718.

Hansson, Mats et al., Cloning and Characterization of the *Bacillus subtilis hemEHY* Gene Cluster, Which Encodes Protoheme IX Biosynthetic Enzymes, Journal of Bacteriology, Dec. 1992, vol. 174, p. 8081-8093.

Kaneko, Tsutomu et al., Acetoin Fermentation by Citrate-Positive *Lactococcus lactis* subsp. *lactis* 3022 Grown Aerobically in the Presence of Henin or $Cu^{2+}$, Applied and Environmental Microbiology, vol. 56, No. 9, Sep. 1990, p. 2644-2649.

Khosla, Chaitan et al., Heterologous Expression of A Bacterial Haemoglobin Improves The Growth Properties of Recombinant *Escherichia coli*, Nature vol. 331, Feb. 18, 1988, pp. 633-635.

Kita, Kiyoshi et al., Terminal Oxidases of *Escherichia coli* Aerobic Respiratory Chain, The Journal of Biological Chemistry, vol. 259, No. 5, Issue of Mar. 10, pp. 3375-3381, 1984.

Leung et al., "Effects of Porphyrins and Inorganic Iron on the Growth of *Prevotella Intermedia*," FEMS Microbiology Letters, 209, published Feb. 22, 2002, 15-21.

Lorence, Robert M. et al., Potentiometric Analysis of the Cytochromes of an *Escherichia coli* Mutant Strain Lacking the Cytochrome d Terminal Oxidase Complex, Journal of Bacteriology, vol. 157, No. 1, Jan. 1984, p. 115-121.

Miller, Michael J. et al., The Purification and Characterization of the Cvtochrome *d* Terminal Oxidase Complex of the *Escherichia coli* Aerobic Respiratory Chain, The Journal of Biological Chemistry, vol. 258, No. 15, Aug. 1983, pp. 9159-9165.

Morishita, Takashi et al., Production of Menaquinones by Lactice Acid Bateria, J. Diary Sci., (1999) 82:1897-1903.

Pugh, Shirley Y. R. et al., *Growth of Streptococcus faecalis var. zymogenes* on Glycerol: The Effect of Aerobic and Anaerobic Growth in the Presence and Absence of Haematin on Enzyme Synthesis, Journal of General Microbiology (1982) 1009-1017.

Ritchy, T.W. et al., Distribution of Cytochrome-like Respiration in Streptococi, Journal of General Microbiology (1976), vol. 93, No. 1, pp. 195-203.

Sattler, Isabel et al., Cloning, Sequencing, and Expression of the Uroporphyrinogen III Methyltransferase *cobA* Gene of *Propionibacterium freudenreichii* (*shermanii*), Journal of Bacteriology, vol. 177, No. 6, Mar. 1995, p. 1564-1569.

Sijpesteijn, Antje Kaars, Induction of Cytochrome Formation and Stimulation of Oxidative Dissimilation by Hemin in *Streptococcus lactis* and *Leuconostoc mesenteroides*, Antonie van Leeuwenhoek, 36 (1970) 335-348.

Skinner F.A. et al., Streptococci, The Society of Applied Bacteriology Symposium Series No. 7, 1978.

Taketani, Shigeru et al., Structure and Transcriptional Regulation of The Mouse Ferrochelatase Gene, GENE, 227(1999)117-124.

von Wachenfeldt, Clacs et al., Molecular Biology of *Bacillus subtilis* Cytochromes, FEMS Microbiology Letters 100 (1992) 91-100.

Winstedt, Lena et al., *Enterococcus faecalis* V583 Contains a Cytochrome *bd*-Type Respiratory Oxidase, Journal of Bacteriology, Jul. 2000, 182:3863-3866.

Worst, Dennis et al., Multiple Haem-Utilization Loci in Helicobacter pylori, Microbiology (1999), 145, 681-688.

Zerr et al., "Growth Stimulation of *Porphyromonas endodontalis* by Hemoglobin and *protoporphyrin IX*," Oral Microbiology and Immunology, 2000, 15: 365-370.

Restriction Requirement mailed Mar. 22, 2001 in U.S. Appl. No. 09/488,644.

Non-Final Office Action mailed Dec. 31, 2002 in U.S. Appl. No. 09/767,680.

Non-Final Office Action mailed Aug. 1, 2003 in U.S. Appl. No. 09/767,680.

Final Office Action mailed Nov. 26, 2004 in U.S. Appl. No. 09/767,680.

Final Office Action mailed Apr. 19, 2005 in U.S. Appl. No. 09/767,680.

Non-Final Office Action mailed Mar. 8, 2006 in U.S. Appl. No. 09/767,680.

Final Office Action mailed Oct. 27, 2006 in U.S. Appl. No. 09/767,680.

Non-Final Office Action mailed Jun. 6, 2007 in U.S. Appl. No. 09/767,680.

Final Office Action mailed Jan. 17, 2008 in U.S. Appl. No. 09/767,680.

Requirement for Restriction/Election mailed Sep. 12, 2002 in U.S. Appl. No. 09/767,680.

Advisory Action before the Filing of an Appeal Brief mailed Nov. 1, 2005 in U.S. Appl. No. 09/767,680.

Advisory Action before the Filing of an Appeal Brief mailed Feb. 14, 2007 in U.S. Appl. No. 09/767,680.

Standard European Search Report from the European Patent Office completed May 10, 2000.

Moss G.P., Nomenclature of Tetrapyrroles. Recommendations 1986 IUPAC-IUB Joint Commission on Biochemical Nomenclature (JCBN) European Journal of Biochemistry, vol. 178, No. 2, pp. 277-328 (1996).

Taber, H.W., Respiratory Chains. In *Bacillus subtilis* and Other Gram Positive Organisms, pp. 190-212—No Date.

Duwat et al., Respiration Capacity of the Fermenting Bacterium *Lactococcus lactis* and iits Positive Effects on Growth and Survival, J. Bacteriol., vol. 183, No. 15, pp. 4509-4516, Aug. 2001.

Noya et al., Heme Compounds as Iron Sources for Nonpathogenic Rhizobium Bacteria, J. Bacteriol., vol. 179, No. 9, pp. 3076-3078.

Gaudu et al., In Lactic Acid Bacteria: Genetics Metabolism and Applications, Proceedings of the Seventh Symposium on Lactic Acid Bacteria, Sep. 1-5, 2002: Respiratory Capacity and Consequences in *Lactococcus lactis*, pp. 263-269.

Nagayasu, et al. (2007) *Journal of Bioscience and Bioengineering* 103(6): 529-534.

McGraw-Hill Dictionary of Scientific and Technical Terms, $5^{th}$ Ed., definition of Starter [MICROBIO], Sybil Parker Editor in Chief, Copyright 1994.

Duwat, et al. (2001) *Journal of Bacteriology* 183: 4509-4516.

Hansen, et al. (2002) *International Journal of Food Microbiology* 78: 119-301.

Lechardeur, et al. (2011) *Current Opinion in Biotechnology* 22: 143-149.

Microbiology Laboratories 12-1 "An Introduction to Lactic Acid Bacteria." (4 pages) [downloaded Aug. 27, 2012].

Rezaïki, et al. (2008) *Molecular Microbiology* 67: 947-957.

* cited by examiner

PORPHYRIN CONTAINING LACTIC ACID BACTERIAL CELLS AND USE THEREOF

Cross Reference to Related Applications

This application is a Divisional of U.S. patent application Ser. No. 09/767,680, filed Jan. 24, 2001, which is a continuation-in-part of U.S. patent application Ser. No. 09/488,644, filed Jan. 21, 2000, now abandoned, and a continuation of International application no PCT/DK01/00036, filed Jan. 18, 2001.

FIELD OF INVENTION

The present invention relates to the field of lactic acid bacterial starter cultures and in particular to culturally modified lactic acid bacterial cells containing a porphyrin compound. More specifically, the invention provides a novel method of reducing the oxygen content in a food and feed product or starting material therefor and means of improving the shelf life and/or quality of such products by using the culturally modified bacterial cells. Thus, such cells are useful in the manufacturing and preservation of food and feed products.

TECHNICAL BACKGROUND AND PRIOR ART

Lactic acid bacteria are used extensively in the food and feed industry in the manufacturing of fermented products including most dairy products such as cheese, yoghurt and butter; meat products; bakery products; wine or vegetable products. When used for such purposes, cultures of lactic acid bacteria are generally referred to as starter cultures and they impart specific features to various fermented products by performing a number of metabolic and other functions herein.

In the present context, the expression "lactic acid bacteria" designates a group of Gram positive, catalase negative, non-motile, microaerophilic or anaerobic bacteria which ferment sugar with the production of acids including lactic acid as the predominantly produced acid, acetic acid, formic acid and propionic acid. The industrially most useful lactic acid bacteria are found among *Lactococcus* species, *Lactobacillus* species, *Streptococcus* species, *Enterococcus* species, *Leuconostoc* species, *Oenococcus* species and *Pediococcus* species.

When lactic acid bacteria are cultivated in a medium like milk or any other starting material in the manufacturing of food and feed products, the medium becomes acidified as a natural consequence of the growth and metabolic activity of the lactic acid bacterial starter cultures. In addition to the production of lactic acid/lactate from citrate, lactose or other sugars several other metabolites such as e.g. acetaldehyde, α-acetolactate, acetoin, acetate, ethanol, carbon dioxide, diacetyl and 2,3-butylene glycol (butanediol) are produced during the growth of the lactic acid bacteria.

Generally, the growth rate and the metabolic activity of lactic acid bacterial starter cultures can be controlled by selecting appropriate growth conditions for the strains of the specific starter culture used such as appropriate growth temperature, oxygen tension and content of nutrients.

Although milk is generally an ideal medium for the growth of lactic acid bacteria, a high content of oxygen in the milk affects the growth of the bacteria adversely and it is known in the dairy industry that a reduction of the oxygen content of the milk raw material may result in a more rapid growth of the added bacteria which in turn results in a more rapid acidification of the inoculated milk. Currently, such a reduction of the oxygen content is carried out by heating the milk in open systems, by deaerating the milk in vacuum or by a sparging treatments. Alternative means of reducing the oxygen content include the addition of oxygen scavenging compounds or the use of mixed cultures comprising two or more lactic acid bacterial species, at least one of which is less sensitive to oxygen.

WO 98/54337 discloses a method of enhancing the growth rate of lactic acid bacteria by cultivating the lactic acid bacteria in association with a metabolically engineered lactic acid bacterial helper organism which has a defect in its pyruvate metabolism, resulting in an increased oxygen consumption by the helper organism. However, this method of reducing the oxygen content in a medium is limited to the use of specific modified lactic acid bacterial strains and thus, there is a need to find a biological method of oxygen reduction in a food or feed starting material which does not involve the use of specifically mutated or metabolically modified lactic acid bacteria.

As mentioned above, when grown anaerobically lactic acid bacterial cells ferment sugars principally to lactic acid/lactate via pyruvate. NADH produced in the cells during this catabolism is reoxidised via lactate dehydrogenase. Under aerobic conditions, however, NADH can partly become reoxidised by NADH peroxidase and oxidase. Thus, under aerobic conditions pyruvate can be converted into other end products than those produced under anaerobic conditions which in turn results in an increase in biomass yield. Most lactic acid bacteria are catalase negative when grown in a haeme or haematin free medium. NADH peroxidase may therefore act to remove $H_2O_2$ produced by aerobic cultures of species unable to form a pseudo-catalase.

It is known that some lactic acid bacteria can form catalase and cytochromes when the aerobic growth medium is supplemented with haematin, blood or a haemoprotein. Sijpesteijn (1970) showed that the fermentation of strains of *Lactococcus lactis* and *Leuconostoc mesenteroides* in the presence of 10 ppm of haemin induced profound changes in the aerobic breakdown of glucose by resting cells of both organisms. This was observed when cells were cultivated under aerobic condition and, in the presence of haemin and glucose, were transferred into a resting cell medium, i.e. a medium wherein the cells are not capable of growth. Furthermore, an increased $O_2$ uptake was observed and less lactic acid and more acetic acid and acetoin was produced. It was shown that cytochromes were formed in these organisms when cultured under the above culture conditions and that the respiration became more sensitive to KCN. It was suggested by this author that, after growth in the presence of haemin, a cytochrome-mediated respiration regulated by haemin was mainly responsible for the oxidation of NADH and that NADH oxidase only played a minor role under these conditions.

In a study on a cytochrome-like system in lactic acid bacteria, Ritchey & Seeley (1976) reported similar results. When grown on a haematin-containing medium with glucose some strains such as strains of *Streptococcus faecalis* or *L. lactis*, e.g. *L. lactis* subsp. *lactis* biovar. *diacetylactis* produced cytochromes whereas *S. faecium* did not. It was stated by these authors that strains like *S. faecalis* or *L. lactis* are blocked in the steps of haeme synthesis but possess the genetic determinants to establish a membrane-bound cytochrome electron transport chain under appropriate condition.

However, Kaneko et al. (1990) could not observe cytochromes when culturing a $Citr^+$ (i.e. citrate metabolising) strain of *L. lactis* under aerobic conditions and in the presence of haemin and/or $Cu^+$. Furthermore, they did not observe any difference in NADH oxidase, diacetyl reductase or lactate dehydrogenase activity when culturing that strain under these culture conditions. However, they observed an increase in the production of diacetyl and acetoin due to an activation of diacetyl synthase by haemin and/or $Cu^+$. Japanese Patent Application JP 04-36180 and EP 430 406<both filed in the name of Meiji Milk Production Co. Ltd., proposed using these culture conditions to improve the production of diacetyl and acetoin by using the $Citr^+$ strain of *L. lactis*.

The above studies all show that the addition of haemin or haematin to the fermentation medium under aerobic conditions results in changes in the aerobic breakdown of glucose and that a possible cytochrome dependent aerobic respiration is induced in strains cultured under the above conditions. However, the above documents do not address the problem of reducing the oxygen content of the milk raw material or any other starting material in order to increase the growth of the added bacteria of a starter culture. Although an increased $O_2$ uptake in resting cell systems under aerobic conditions in the presence of haemin and glucose has been reported, the ability of such cultured strains to be used in a starter culture for the manufacturing of a food or feed product has not been suggested.

The present invention is based on the discovery that lactic acid bacterial strains, when cultured or fermented under aerobic conditions in the presence of haemin and other porphyrin compounds, are capable of maintaining their increased oxygen reducing activity/capability when inoculated into milk or any other media under appropriate conditions and without addition of a porphyrin compound. It is thus possible to provide a generally applicable biological method for reducing the oxygen content in milk or any other food or feed starting material, whereby the growth and metabolic activity of lactic acid bacterial starter cultures herein can be substantially enhanced. It is therefore a primary objective of the present invention to provide such a method and culturally modified cells, which are useful in such a method.

Accordingly, these findings have opened up for a novel approach for providing useful culturally modified lactic acid bacterial starter cultures, which approach is based on relatively simple classical fermentation methods and which does not involve genetic engineering or classical mutagenesis. From a practical technological point of view this is advantageous, since the use of genetic engineering or classical mutagenesis in the construction of new strains is very labour intensive and costly and the use of genetically modified organisms in food production may give rise to consumer concerns.

SUMMARY OF THE INVENTION

Accordingly, the present invention provides in a first aspect a culturally modified lactic acid bacterial cell that has, relative to the cell from which it is derived, an increased content of a porphyrin compound.

In a further aspect there is provided a starter culture composition comprising the culturally modified lactic acid bacterial cell according to the invention.

In another aspect, there is provided a method of reducing the oxygen content in a food or feed product or in a food or feed product starting material, the method comprising adding to the product or to the starting material an effective amount of the culturally modified lactic acid bacterial cells according to the invention or the above starter culture composition.

In yet another aspect, there is provided a method of improving the shelf life and/or the quality of an edible product, comprising adding to the product an effective amount of the culturally modified lactic acid bacterial cells according to the invention or the above starter culture composition.

In a still further aspect, the invention pertains to a method of preparing a fermented food or feed product, comprising adding an effective amount of the culturally modified lactic acid bacterial cell according to the invention or the above composition to a food or feed product starting material, wherein the cell or the composition is capable of fermenting said starting material to obtain the fermented food or feed.

The invention pertains in other aspects to the use of the above modified lactic acid bacterial cell or the composition comprising such cells for the production of a metabolite or for the production of a bacteriocin.

DETAILED DISCLOSURE OF THE INVENTION

It is a primary objective of the present invention to provide a generally applicable biological method of reducing the oxygen content in a food or feed product or in a starting material for such products. Accordingly, in one aspect there is provided a culturally modified lactic acid bacterial cell that has, relative to the cell from which it is derived, an increased content of a porphyrin compound.

As used herein the expression "culturally modified lactic acid bacterial cell" relates to a cell of a lactic acid bacterium which has been cultured by fermentation in an appropriate nutrient medium in which an effective amount of at least one porphyrin compound is present. In the present context, the expression "an effective amount" means an amount that is sufficient to cause the lactic acid bacterium to become modified as defined herein. It will be understood from the discussion above, that the presence of the porphyrin compound causes the cells cultured under such conditions to have a modified aerobic breakdown of carbohydrates, such as lactose, glucose or galactose. After fermentation the bacterial cells are harvested using conventional procedures and subsequently used as a starter culture for the inoculation of a milk medium or any another starting material for food or feed manufacturing wherein the cells are capable of replicating, with or without the addition of a porphyrin compound to the medium. As used herein, the term "fermentation" refers to a process of propagating or cultivating a lactic acid bacterial cell under both aerobic and anaerobic conditions.

As shown in the below examples, it was possible for the inventors of the present invention to detect the presence and the amount of a porphyrin compound in cells which have been cultured in the presence of a porphyrin compound both when analysing the culturally modified cells after fermentation or after the cells have been transferred to a medium wherein the cells are capable of replicating. It was surprising when the inventors observed that the addition of a porphyrin compound to the culture medium results in an increased content of the porphyrin compound in the culturally modified cells relative to the cells from which they are derived. It will be appreciated that the expression "relative to the cells from which they are derived" relates to similar lactic acid bacterial cells, which, in contrast to the culturally modified bacterial cells according to the invention, were not cultured in a medium containing a porphyrin compound.

Thus, in a preferred embodiment, the cell according to the invention contains at least 0.1 ppm on a dry matter basis of a porphyrin compound, including at least 0.2 ppm, such as at least 0.5 ppm, including at least 1 ppm, e.g. at least 2 ppm, such as at least 5 ppm, including such as 10 ppm, such as at least 20 ppm, e.g. at least 30 ppm, such as at least 40 ppm, e.g. at least 50 ppm, such as at least 60 ppm, e.g. at least 70 ppm, such as at least 80 ppm, e.g. at least 90 ppm, such as at least 100 ppm on a dry matter basis of a porphyin compound.

"Porphyrin compounds" refers in the present context to cyclic tetrapyrrole derivatives, whose structures are derived from that of porphyrin by substitution at the carbon atoms located at the apices of the pyrrole core, with various functional groups. It also refers to complexes of said derivatives with a metal atom that forms coordinate bonds with two of the four nitrogens of the porphyrin ring. The definition encompasses also, but is not limited to, uroporphyrins, coproporphyrins, protoporphyrins and haematoporphyrins including their salts and esters and their complexes with a metal atom, preferably an iron atom, the dihydrochloride of coproporphyrin I, the tetraethyl ester of coproporphyrin III, the disodium salt of protoporphyrin IX, the dichloride of haematoporphyrin IX, the tetraisopropyl ester or the tetramethyl ester of coproporphyrin, the tetraisopropyl ester or the tetramethyl ester of coproporphyrin III, haematoporphyrin IX, haemoglobin, protoporphyrin IX, the dimethyl ester of protoporphyrin IX, zinc protoporphyrin IX, haematin and cytohaemin. Particularly preferred porphyrin compounds are protoporphyrin IX and its complexes with an iron atom, in particular haeme and haemin. Furthermore, the definition encompasses various chlorophylls, such as chlorophyll a and chlorophyll b, their derivatives such as chlorophyllins and also their salts and esters, and their complexes with a metal atom, such as an iron, copper or magnesium atom.

As it is further shown in the below examples, when using the HPLC-MS method the inventors observed in cells grown on a nutritional medium containing a porphyrin compound both under anaerobic and aerobic conditions clear peaks in the porphyrin region. No cytochromes were detected in cells cultured in a medium without haemin. However, it has been found that it is possible to detect cytochromes at a relatively high level in the modified cells after they have been transferred to a medium wherein the cells are capable of replicating. This is a very surprising finding, as it has not hitherto been shown that lactic acid bacterial cells grown under aerobic conditions in the presence of a porphyrin compound has an increased content of cytochromes and that the culturally modified cells contain cytochromes after inoculation into a medium wherein the cells are capable of replicating. Without intending to limit the invention in any way, the inventors propose that a bacterial cell grown under aerobic conditions may, through the action of an NADH oxidase, regenerate the required $NAD^+$ under oxygen consumption. If a porphyrin compound is present in the culture medium under aerobic conditions the bacterial cells produce cytochromes and, due to the cytochrome dependent respiration, oxygen is reduced to water with the formation of metabolically usable energy, such as ATP and $NAD^+$.

It will be understood that, although the formation of cytochromes in lactic acid bacterial cells is induced by the presence of a porphyrin compound, it is possible to observe cells grown under such conditions having, relative to the cells from which they are derived, an increased content of a porphyrin compound without the formation of cytochromes. Thus, it is possible to detect and measure in the lipid membranes of the modified cells according to the invention both free haemin, haemin bound to a non-cytochrome protein and haemin bound to a cytochrome protein to form a complex. In addition, it is possible to observe in the cytoplasm of the modified cells both free cytoplasmic haemin, cytoplasmic haemin bound to a non-cytochrome protein and cytoplasmic haemin bound to a cytochrome protein to form a complex.

In the present context the term "cytochrome" relates to a group of electron-transporting proteins containing a haeme prosthetic group and thus to components of the respiratory and photosynthetic electron transport chains, in which the haeme iron exits in oxidised or reduced state. The definition encompasses, but is not limited to, cytochromes of a-, b-, c-, d- or o-types and combinations of these cytochrome types as e.g. mentioned in Wachenfeldt & Hederstedt (1992). It will be understood, that the term "the respiratory electron transport chain" refers to either an aerobic respiratory electron transport chain functioning with molecular oxygen as terminal electron acceptor, or an anaerobic respiratory electron transport chain functioning with other terminal electron acceptors than molecular oxygen such as nitrate, sulphate, fumarate or trimethylamine oxide.

Thus, in a preferred embodiment, the cells according to the invention contain at least 0.1 ppm on a dry matter basis of a cytochrome, including at least 0.2 ppm, such as at least 0.5 ppm, including at least 1 ppm, e.g. at least 2 ppm, such as at least 5 ppm, including such as 10 ppm, such as at least 20 ppm, e.g. at least 30 ppm, such as at least 40 ppm, e.g. at least 50 ppm, such as at least 60 ppm, e.g. at least 70 ppm, such as at least 80 ppm, e.g. at least 90 ppm, such as at least 100 ppm on a dry matter basis of a cytochrome.

In accordance with the invention, any starter culture organisms which are of use in the food or feed industry, including the dairy industry, can be used. Thus, the cells can be selected from a lactic acid bacterial species including *Lactococcus* spp., *Lactobacillus* spp., *Leuconostoc* spp., *Pediococcus* spp., *Streptococcus* spp., *Propionibacterium* spp., *Bifidobacterium* spp. and *Oenococcus* spp. In a specific embodiment the cells are of *Lactococcus lactis*, including *Lactococcus lactis* subsp. *lactis* strain CHCC373 deposited under the accession number DSM 12015.

Although it is a primary objective of the present invention to provide a generally applicable biological method for reducing the oxygen content in milk or any other starting material, i.e. without the use of genetically engineered or mutated organisms, it will be appreciated that the modified bacteria of the invention may also be a previously genetically modified strain of one of the above lactic acid bacterial strains or any other starter culture strain. As used herein the expression "genetically modified bacterium" is used in the conventional meaning of that term i.e. it includes strains obtained by subjecting a lactic acid bacterial strain to any conventionally used mutagenization treatment including treatment with a chemical mutagen such as ethanemethane sulphonate (EMS) or N-methyl-N'-nitro-N-nitroguanidine (NTG), UV light or to spontaneously occurring mutants. Furthermore, it is possible to provide the genetically modified bacteria by random mutagenesis or by selection of spontaneously occurring mutants, i.e. without the use of recombinant DNA-technology and it is envisaged that mutants of lactic acid bacteria can be provided by such technology including site-directed mutagenesis and PCR techniques and other in vitro or in vivo modifications of specific DNA sequences once such sequences have been identified and isolated.

It was, as mentioned above, very surprising, when the inventors found that cells of lactic acid bacterial strains, when they are cultured or fermented under aerobic conditions in the presence of a porphyrin compound, become capable of maintaining their increased capability to reduce oxygen, obtained during the fermentation, when they are inoculated into milk or any other non-porphyrin-containing or low-porphyrin-containing starter material under appropriate conditions. However, it is also possible to observe this ability when such culturally modified cells are inoculated in a medium wherein a porphyrin compound is added. Furthermore, the inventors were able to show that the aerobic breakdown of lactose resulted in an increased $O_2$ uptake.

Thus, in a preferred embodiment of the present invention, the culturally modified lactic acid bacterial cells are cells which, when they are inoculated at a concentration of about $10^7$ cells/ml into low pasteurised skimmed milk having 8 ppm of dissolved oxygen and leaving the milk to stand for about 2 hours at a temperature of about 30° C. consumes at least 25% of the oxygen.

However, the culturally modified lactic acid bacterial cells according to the invention may be particularly useful when the cells under the above conditions consumes at least 30% of the oxygen present in the milk, including at least 40%, such as at least 50%, e.g. at least 60%, such as at least 70%, e.g. at least 80%, such as at least 90%, e.g. at least 95% of the dissolved oxygen.

It has been found that a culturally modified lactic acid bacterial cell according to the invention has, relative to the cell from which it is derived, an altered NADH oxidase, i.e. NOX activity, and/or lactate dehydrogenase (LDH) activity. As explained above, cells grown under aerobic condition may be capable of regenerating the required energy from other systems induced during aerobic fermentation and maintained during the inoculation of the cells into milk or any other non-porphyrin-containing or low-porphyrin-containing starter material. Thus, in preferred embodiments of the present invention the culturally modified cell is a cell which, relative to the cell from which it is derived, has a decreased NOX activity and/or a decreased LDH activity. It will be understood that the NOX enzyme, which is encoded by the nox gene, is one example of an $H_2O$ forming NADH oxidase. This enzyme regenerates two equivalents of $NAD^+$ under consumption of molecular oxygen. Further examples of NADH oxidases which could be present in a cell according to the invention are non-haeme flavoproteins where two types have been reported, one which catalyses the reduction of $O_2$ to $H_2O_2$, the other one the reduction of $O_2$ to $H_2O$.

Accordingly, in further embodiments of the present invention, the culturally modified cell has a NOX activity which is decreased by at least 10%, 20%, 30%, 40%, 50%, 60%, 75%, or 95% relative to the cell from which it is derived. In an interesting embodiment, the modified cell has a NOX activity which is decreased by about 100% relative to the cell from which it is derived, i.e. the NOX activity is essentially absent in that modified cell.

In still further embodiments, the culturally modified cell has a LDH activity which is decreased by at least 10%, including at least 20%, 30%, 40%, 50%, 60%, 75% or 95% relative to the cell from which it is derived. In an useful embodiment, the modified cell has a LDH activity which is decreased by about 100% relative to the cell from which it is derived, i.e. the LDH activity is essentially absent in that modified cell.

The culturally modified lactic acid bacterial cells according to the invention are useful as starter cultures in the production of food and feed products. Accordingly, in a further aspect, the invention relates to a starter culture composition comprising the culturally modified lactic acid bacterial cell according to the invention having, relative to the cell from which it is derived, an increased content of a porphyrin compound.

It is convenient to provide the starter culture composition according to the invention as a starter culture concentrate both when used in food and feed production or for the production of metabolites that are generated by the starter culture strains. Typically, such a concentrate contains cells of the starter culture organisms as a non-concentrated fermentate of the respective starter culture strain(s) or in a concentrated form. Accordingly, the starter culture composition of the invention may have a content of viable cells (colony forming units, CFUs) which is at least $10^4$ CFU/g including at least $10^5$ CFU/g, such as at least $10^6$ CFU/g, e.g. at least $10^7$ CFU/g, $10^8$ CFU/g, $10^9$ CFU/g, $10^{10}$ CFU/g or $10^{11}$ CFU/g of the composition.

The starter culture composition according to the invention can be provided as a liquid, frozen or dried, such as e.g. freeze-dried or spray-dried, starter culture composition.

As it is normal in lactic acid bacterial fermentation processes to apply mixed cultures of lactic acid bacteria, the composition according to the invention comprises in certain embodiments a multiplicity of strains either belonging to the same species or belonging to different species. Accordingly, in a further embodiment, the starter culture composition comprises cells of two or more different lactic acid bacterial strains. A typical example of such a useful combination of lactic acid bacterial cells in a starter culture composition is a mixture of the culturally modified lactic acid bacterial cell according to the invention and one or more *Lactococcus* spp. such as *L. lactis* subsp. *lactis* or *L. lactis* subsp. *lactis* biovar. *diacetylactis* or *Leuconostoc* spp. Such a mixed culture can be used in the manufacturing of fermented milk products such as buttermilk and cheese. Another example is a mixture of *Streptococcus thermophilus* and *Lactobacillus delbrueckii* subsp. *bulgaricus*.

In one embodiment, the composition according to the invention is a composition which further comprises at least one component that enhances the viability of the bacterial cell during storage, including a bacterial nutrient, a vitamin and/or a cryoprotectant. In the case of a composition subjected to a freezing step, a suitable cryoprotectant is selected from the group consisting of glucose, lactose, raffinose, sucrose, trehalose, adonitol, glycerol, mannitol, methanol, polyethylene glycol, propylene glycol, ribitol, alginate, bovine serum albumin, carnitine, citrate, cysteine, dextran, dimethyl sulphoxide, sodium glutamate, glycine betaine, glycogen, hypotaurine, peptone, polyvinyl pyrrolidine and taurine. The cryoprotectant used is advantageously selected from alginate, glycerol, glycine betaine, trehalose and sucrose.

In accordance with the invention, there is also provided a method of reducing the oxygen content in a food or feed product or in a food or feed product starting material, which method comprises adding to the product or to the starting material an effective amount, e.g. in the form of a suspension, of the culturally modified lactic acid bacterial cells according to the invention or a starter culture composition according to the invention.

Industrial production of edible products typically includes process steps such as mixing, pumping or cooling whereby the degree of oxygen saturation of the edible product is increased and, as a result, the edible product starting material may have a relatively high initial oxygen content (high degree of oxygen saturation) which is unfavourable for lactic acid bacterial starter cultures. It has now surprisingly been found that when a suspension of the culturally modified lactic acid bacterial cells according to the invention or a starter culture composition of this invention is cultivated in an edible food or feed product starting material having an initial degree of oxygen saturation of at least 8%, e.g. 10% or higher such as 20% or higher, the starter culture is capable of reducing the oxygen content in the starting material to a content, which is favourable for lactic acid bacterial starter cultures.

In the present context, the expression "reducing the oxygen content" refers to the capability of the suspension of the culturally modified lactic acid bacterial cells containing a porphyrin compound or the starter culture composition according to the invention to reduce the initial content of the oxygen in a medium not supplemented with porphyrin compound.

In useful embodiments of the method of the present invention the culturally modified lactic acid bacterial cells or the starter culture composition according to the invention is one, which is capable of reducing the amount of oxygen present in the medium by at least 1% per hour including by at least 10% per hour, such as by at least 20% per hour, e.g. by at least 30% per hour. The reduction may even be by at least 40% per hour including by at least 50% per hour, such as by at least 60% per hour, e.g. by at least 70% per hour, such as by at least 80% or by at least 90% per hour.

In a specific embodiment of the method according to the invention the lactic acid bacterial starter culture is a mixed strain culture comprising at least two strains of lactic acid bacteria. Examples of such mixed strain cultures are described above. Thus, in particularly preferred embodiments of the invention the culturally modified cells, when inoculated as a mixed culture comprising cells of at least one further culture strain which was not cultivated under aerobic conditions in the presence of a porphyrin compound, are capable of enhancing the growth rate of that further lactic acid bacterial culture strain. Growth conditions, which are in all respects optimal for all strains of such lactic acid bacterial mixed strain cultures, may not be found. Therefore, the metabolic activity of a mixed strain culture may be controlled selectively by choosing a temperature which favours an increased production of desired metabolites by one or more strains, but which on the other hand may result in a decreased production of other metabolites by other strains. However, the overall result of cultivating a lactic acid bacterial mixed strain culture with the culturally modified cell according to the invention as compared to the lactic acid bacterial mixed strain culture being cultivated alone is an increased number of cells, an increased production of one or more metabolites, including acids and aroma compounds and/or a decreased production of one or more metabolites.

Evidently, the above-mentioned enhanced production of acids of the lactic acid bacterial starter culture will result in a pH decrease of the medium inoculated with the culturally modified cells of the invention which exceeds that obtained in the same medium inoculated with the starter culture alone. The difference in pH of the medium inoculated with the starter culture alone and the medium inoculated with the starter culture in association with a suspension of the cell according to the invention is referred to herein as $\Delta pH$. In useful embodiments of the present method the enhanced acid production results in a $\Delta pH$ of at least 0.05 after 3 hours or more of cultivation, such as a $\Delta pH$ of at least 0.1 after 3 hours or more of cultivation, e.g. a $\Delta pH$ of at least 0.5 after 3 hours or more of cultivation, such as a $\Delta pH$ of at least 0.8 after 3 hours or more of cultivation, e.g. a $\Delta pH$ of at least 1.0 after 3 hours or more of cultivation.

In preferred embodiments of the present invention the ratio between culturally modified cells and non-modified lactic acid bacterial starter culture cells is in the range of 1000:1 to 1:1000 such as 500:1 to 1:500, e.g. 100:1 to 1:100, such as in the range of 50:1 to 1:50, e.g in the range of 20:1 to 1:20, such as in the range of 10:1 to 1:10 or in the range of 5:1 to 1:5 such as in the range of 2:1 to 1:2.

In further embodiments of the present method the amount of culturally modified cells is in the range of $10^3$ to $10^{12}$ CFU per g starting material. Accordingly, the modified cells are added in amounts which result in a number of viable cells which is at least $10^3$ colony forming units (CFU) per g of the edible product starting material, such as at least $10^4$ CFU/g including at least $10^5$ CFU/g, such as at least $10^6$ CFU/g, e.g. at least $10^7$ CFU/g, such as at least $10^8$ CFU/g, e.g at least $10^9$ CFU/g, such as at least $10^{10}$ CFU/g, e.g. at least $10^{11}$ CFU/g of the starting material.

In useful embodiments, the starting material is a starting material for an edible food product including milk, a vegetable material, a meat product, a must, a fruit juice, a wine, a dough and a batter. As used herein, the term "milk" is intended to mean any type of milk or milk component including e.g. cow's milk, human milk, buffalo milk, goat's milk, sheep's milk, dairy products made from such milk, or whey.

In further embodiments, the starting material is a starting material for an animal feed such as silage e.g. grass, cereal material, peas, alfalfa or sugar-beet leaf, where bacterial cultures are inoculated in the feed crop to be ensiled in order to obtain a preservation hereof, or in protein rich animal waste products such as slaughtering offal and fish offal, also with the aims of preserving this offal for animal feeding purposes.

Yet another significant embodiment of the method according to the present invention is where the culturally modified bacterial cells is derived from a bacterial culture generally referred to as a probiotic culture. By the term "probiotic" is in the present context understood a microbial culture which, when ingested in the form of viable cells by humans or animals, confers an improved health condition, e.g. by suppressing harmful microorganisms in the gastrointestinal tract, by enhancing the immune system or by contributing to the digestion of nutrients.

As it is described above, the culturally modified lactic acid bacterial cells containing a porphyrin compound or the starter culture composition according to the invention are capable of reducing the amount of oxygen in a medium. It has been found that such strains can improve the shelf life of edible products, due to their oxygen reducing ability.

Accordingly, it is another objective of the invention to provide a method of improving the shelf life and/or the quality of an edible product, the method comprising adding to the product an effective amount of a suspension of the culturally modified lactic acid bacterial cells according to the invention or a starter culture composition according to the invention. As used herein the term "shelf life" indicates the period of time in which the edible product is acceptable for consumption.

The above shelf life improving effect can be obtained in a variety of edible product components or ingredients such as milk including non-pasteurised (raw) milk, meat, flour dough, wine and plant materials, such as vegetables, fruits or the above mentioned fodder crops.

It is also an objective of the present invention to provide a method of preparing a fermented food or feed product based on the use of the culturally modified lactic acid bacterial strain according to the invention. In its broadest aspect, such method comprises that an effective amount of the culturally modified lactic acid bacterial cells according to the invention or a composition comprising the modified cells are added to a food or feed product starting material, wherein the cells or the composition is capable of fermenting said starting material to obtain the fermented food or feed. It will be appreciated that in such a method one or more strains of non-metabolically modified lactic acid bacteria can be used in addition to the modified lactic acid bacteria.

Useful food product starting materials include any material which is conventionally subjected to a lactic acid bacterial fermentation step such as milk, vegetable materials, meat products, fruit juices, must, wines, doughs and batters. In further embodiments, the resulting fermented food product in the method of the invention is a dairy product such as cheese and buttermilk. In still further embodiments, the starting material is a starting material for an animal feed such as silage e.g. grass, cereal material, peas, alfalfa or sugar-beet leaf.

It is yet another objective of the invention to provide the use of the culturally modified lactic acid bacterial cells of the invention or the composition comprising such cells for the production of a metabolite produced by the cell or the composition. In the present context "produced by the cell or the composition" implies that the metabolite can be one that is naturally produced by the cells or that the metabolite is produced recombinantly by the modified cells. In an alternative embodiment, the production of the metabolite is achieved by co-cultivating a modified cell of the invention with at least one non-modified organism capable of producing the metabolite. Typical examples of metabolites that is produced by the cells include lactic acid, acetaldehyde, α-acetolactate, acetoin, acetate, ethanol, diacetyl and 2,3-butylene glycol.

Additionally, the cells of the invention and compositions comprising such cells are useful for the production of bacteriocins produced naturally or recombinantly by the cells or another, non-modified cell that is co-cultivated with the modified cell of the invention, such as e.g. nisin, reuterin and pediocin.

The invention will now be described in further details in the following non-limiting examples and the drawings wherein FIG. 1a shows the chromatogram of a haemin (ferriprotoporphyrin IX chloride) standard 10 µg/ml. Haemin is eluting after 33.3 min;

Figure 6A:
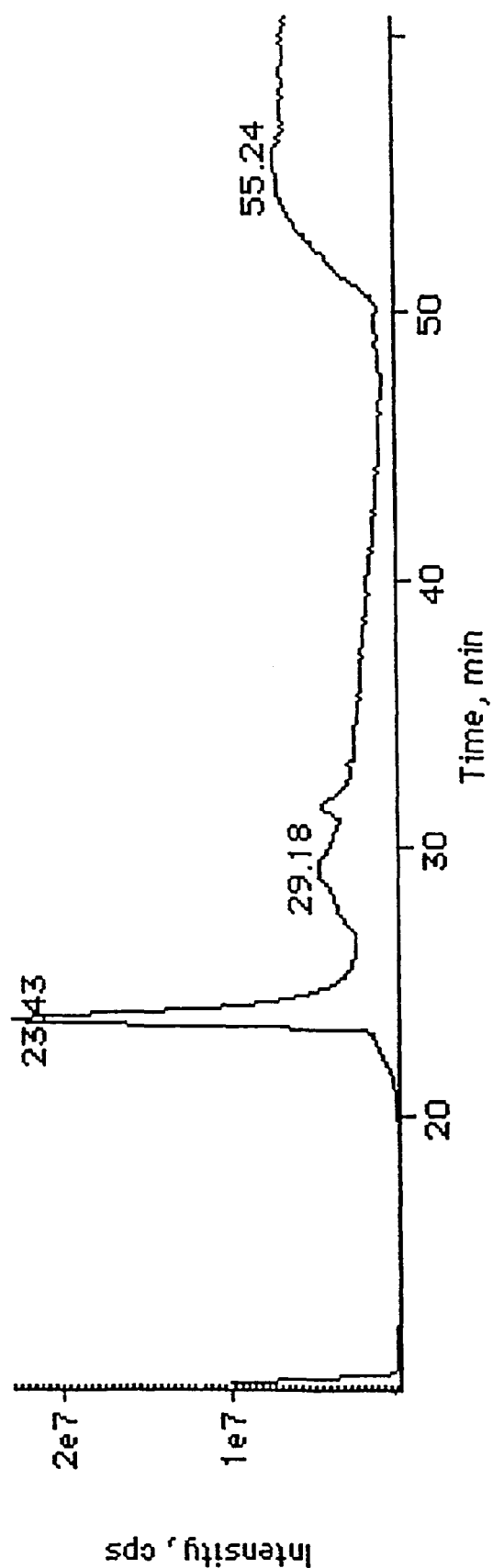
FIG. 6a shows the chromatogram of a Cytochrome c standard 100 µg/ml. Cytochrome c is eluting after 23.4 min.
Figure 6B:
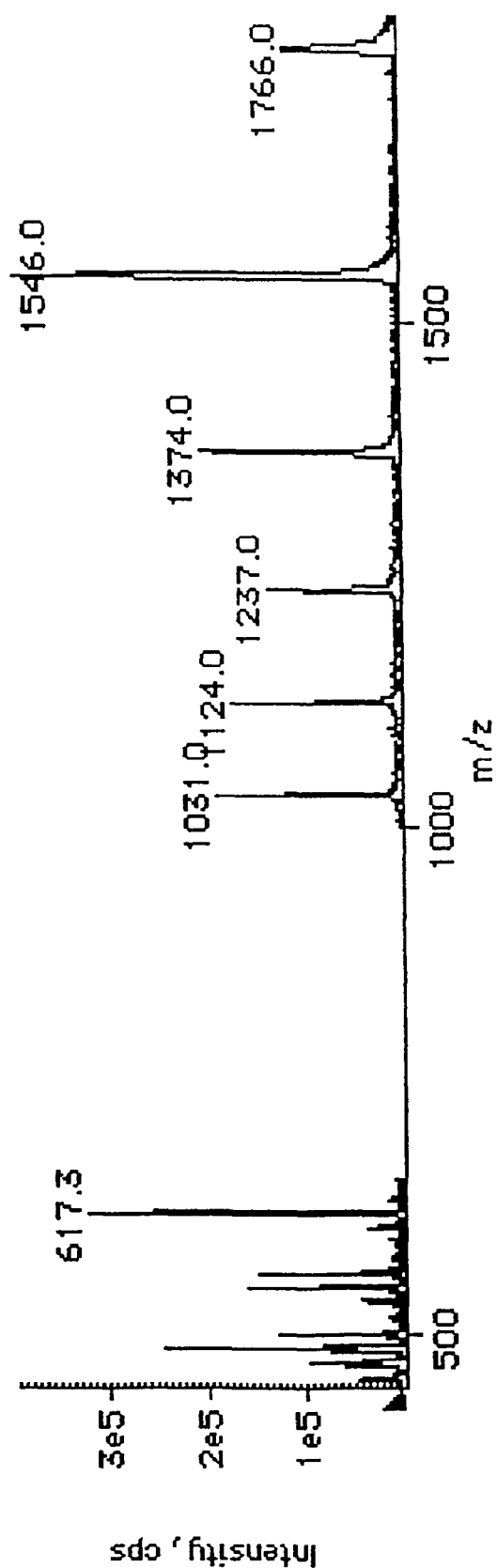
Figure 7:
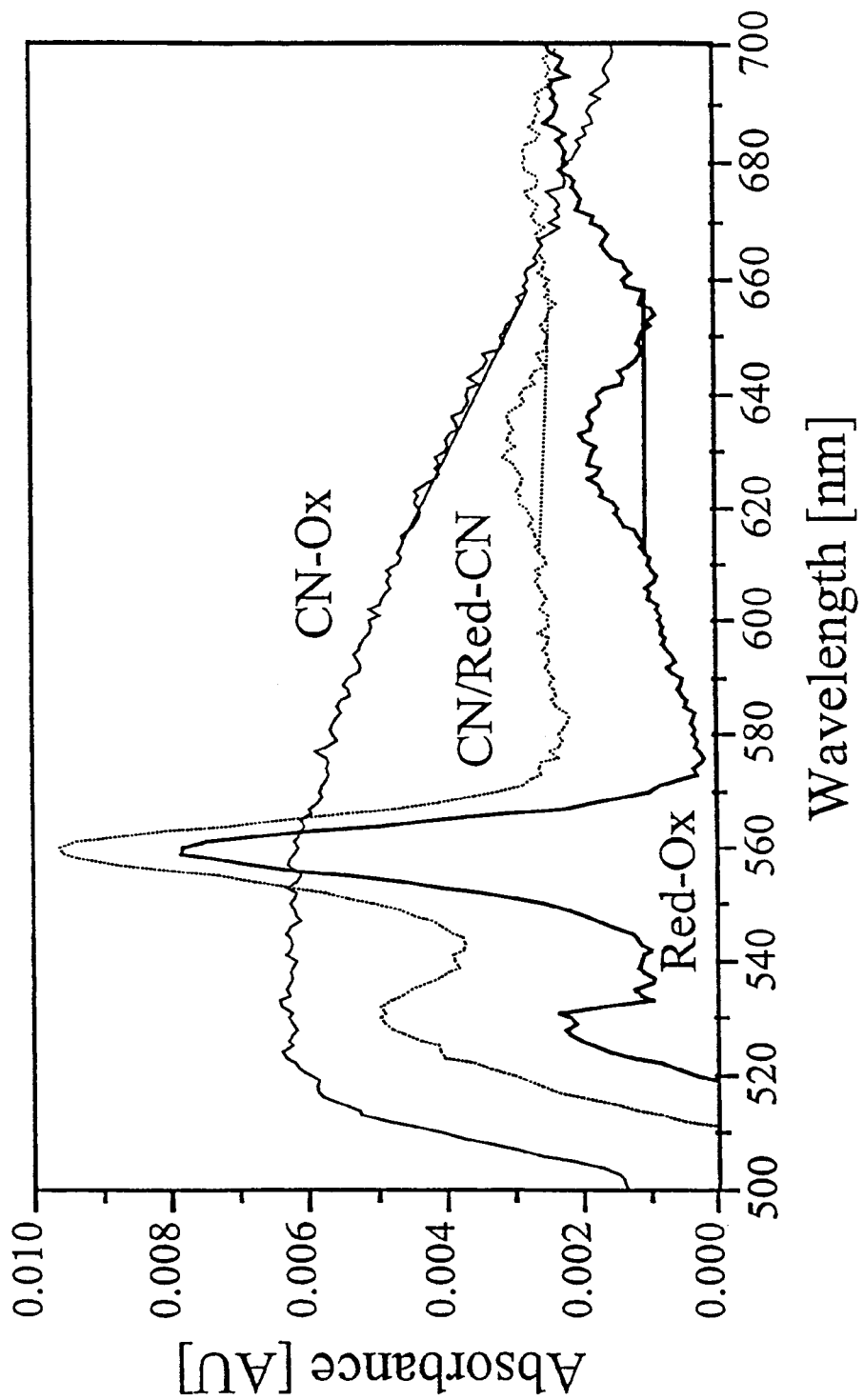

FIG. 6b shows the spectrum of the peak at time 23.4 min in FIG. 6a. The molecular ion of ironporphyrin IX is seen at m/z 617.3 as well as the multiple charged intact protein (m/z 1031; 1124; 1237; 1374; 1546; 1766) with an estimated molecular weight of 12356 Da; and FIG. 7 shows the CN-Ox (thin line), the CN/Red-CN (dashed line) and the Red-Ox (thick line) spectra for cells harvested from fermentation E described in Experiment 2 below.

EXAMPLE 1

A Study of the Effect of the Addition of Haemin to the Fermentation Medium on the Enzyme and Oxygen Content Reducing Activities of a Lactic Acid Bacterium The effect of the addition of haemin to the fermentation medium on the enzyme activity and the oxygen content reducing activity of a lactic acid bacterial strain was studied in two experiments, Experiment 1 and Experiment 2. Furthermore, the presence of haemin and cytochromes in lactic acid bacterial cells when grown in a medium containing haemin was studied.

EXPERIMENT 1

1. Materials and Methods
1.1 Microorganism

The wild type strain *Lactococcus lactis* subsp. *lactis* CHCC373 (from the Chr. Hansen Culture Collection) was applied in this experiment. A sample of the strain was deposited in accordance with the Budapest Treaty with the Deutsche Sammlung von Mikroorganismen und Zellkulturen (DSMZ), Marscheroder Weg, 1b, D-38124 Braunschweig on 17 Feb. 1998 under the Accession No. DSM 12015.

1.2 Medium Composition

The fermentation medium had the following composition: Casein peptone, 30 g/l; Primatone, 30 g/l; soy peptone, 30 g/l; yeast peptone, 15 g/l; $MgSO_4$, 1.5 g/l; Na-ascorbate, 3 g/l; and lactose, 30 g/l. Antifoam (Dow Corning 1510) was added at a concentration of 0.25 g/l.

The medium was sterilised by UHT-treatment. The finished medium had a pH of 6.5.

A fresh solution of haemin was prepared as follows: 1 gram of haemin (Fluka prod. no. 51280, molecular weight 651.96 g/mol) was dissolved in 1 ml 6.7 N $NH_4OH$ and water was added to a final volume of 1 litre. The solution was subsequently autoclaved at 121° C. for 20 min. The haemin was added to fermentations B and D as described in the following at a final concentration of 10 mg/l.

1.3 Fermentation Conditions

A series of four fermentations with the strain CHCC373 was carried out using the fermentation medium defined above:

Fermentation A—Anaerobic fermentation
Fermentation B—Anaerobic fermentation with haemin addition
Fermentation C—Aerobic fermentation
Fermentation D—Aerobic fermentation with haemin addition The fermentations were inoculated with a concentrated cell suspension of CHCC373.

The anaerobic fermentations were run with nitrogen in headspace whereas the aerobic fermentations were sparged with air at a rate of 0.3 litres per minute per litre of fermentation volume (at this level of aeration, the dissolved oxygen concentration was maintained above 65% of saturation level throughout the aerobic fermentations).

All four fermentations were run at a temperature of 30° C. and with a headspace pressure of about 2 bar. The cultures were allowed to acidify to pH 6.2. The pH was subsequently maintained at 6.2 by controlled addition of 13.4 N $NH_4OH$.

Samples of 10 ml were collected throughout the fermentations for measurements of the optical density using a Hitachi U-1100 Spectrophotometer at 600 nm, and subsequent determination of oxygen reducing effect. The samples were stored at −50° C. until analysis.

When no further base consumption was observed, the respective culture was cooled to about 10° C.

1.4 Downstream Processing

Following cooling, each of the four fermentation broths A-D were concentrated by centrifugation and subsequently frozen as pellets in liquid nitrogen. The frozen pellets were stored at −80° C. until further analysis.

1.5 Sample Preparation

About 10 g of frozen pellets from each fermentation was weighed out accurately. These pellets were washed twice in cold 40 ml 0.05 M Na-phosphate buffer (pH 6.1). Following each step of washing the suspensions were centrifuged at 9,000 rpm (Sorvall centrifuge with SS-34 rotor) for 20 min at 4° C.

Following the second wash, the cells were resuspended in 20 ml cold 0.05 M Na-phosphate buffer (pH 6.1). The suspensions were sonicated on ice using a Branson Sonifier 250 at the following parameters: timer, 4 cycles of each 5 min (each cycle followed by cooling to prevent excessive heating of the suspensions); output control, 2; and duty cycle, 30%).

The resulting sonicated cell material was centrifuged at 6,000 rpm (Sorvall centrifuge with SS-34 rotor) for 25 min at 4° C. The supernatants (cell-free extracts) and pellets (cell debris) were separated and stored at −20° C. until enzymatic characterisation and analysis for presence of intracellular haemin.

1.6 Enzymatic Characterisation

The enzymatic assays were all performed at 30° C. using a Secomam Anthelie spectrophotometer provided the Winelie software (ver. 1.50). The cell-free extracts were thawed on ice.

1.6.1 Measurement of NADH Oxidase Activity

NADH oxidase activity of the cell-free extracts was measured by monitoring the oxidation of NADH at 340 nm in a reaction mixture having the following composition: 50 mM Tris-acetate buffer (pH 6.0), 0.5 mM fructose-1,6-diphosphate and 0.5 mM NADH.

1.6.2 Measurement of Lactate Dehydrogenase Activity

Lactate dehydrogenase activity of the cell-free extracts was measured by monitoring the oxidation of NADH at 340 nm in a reaction mixture having the following composition: 50 mM Tris-acetate buffer (pH 6.0), 0.5 mM fructose-1,6-diphosphate, 25 mM pyruvate and 0.5 mM NADH.

The lactate dehydrogenase activity was subsequently corrected for NADH oxidase activity.

One unit of enzyme activity (U) is defined as the activity required for oxidising 1 µmol of NADH per minute.

1.6.3 Protein Determination

For measuring the protein concentration of the cell-free extract, the Bicinchoninic acid (BCA) assay (Pierce, Rockford, USA) was used with Albumin Standard (Pierce) as protein standard.

1.7 Method of Measuring Oxygen Content Reducing Effect

Samples collected during the fermentations were thawed and analysed for their capacity to remove oxygen from milk (low pasteurised skimmed milk). This oxygen reducing effect was assayed in the milk at 30° C.

For each fermentation sample, the oxygen content of the milk was measured regularly by a M0128 Dissolved Oxygen Meter (Mettler Toledo) following inoculation. The initial oxygen concentration of the milk was 8.3 mg/kg.

1.8 Analysis of Porphyrins and Cytochromes

1.8.1 Sample Preparation

Supernatant of Sonicated Cells

To 190 µl of the clear supernatant (cell-free extract) was added 5 µl 3% hydrochloric acid to arrest enzymatic activity, and the sample was analysed using HPLC-MS.

Pellet (Cell Debris)—Procedure A

About 60 mg (weighed accurately) of the pellet was weighed into an Eppendorf tube. 1 ml 88% formic acid was added and the tube was whirly mixed. The suspension was left for 60 min at ambient temperature in order to extract cytochromes and porphyrins from the cells. The tube was centrifuged (6 min at 10,000 rpm using an Eppendorf centrifuge 5415) and the supernatant analysed by HPLC-MS.

Pellet (Cell Debris)—Procedure B

About 250 mg (weighed accurately) of the pellet was weighed into a 10 ml plastic tube. 4 ml 88% formic acid was added and the tube was whirly mixed. The suspension was left for 60 min at ambient temperature in order to extract cytochromes and porphyrins from the cells. The sample was distributed into 4 Eppendorf tubes which were centrifuged for 6 min at 10,000 rpm using an Eppendorf centrifuge 5415. 90 µl aliquots of the supernatant was mixed with 10 µl standard haemin solution with varying haemin concentrations rendering a final concentration of added haemin of 0; 0.2; 0.5 and 1.0 ppm, respectively. The samples were whiny mixed and analysed by HPLC-MS. The area of the specific haemin signal was used for the quantification.

The dry-matter content of the cell debris was determined using a Mettler PM480 Delta Range balance equipped with a Mettler LP-16 drying device (mode: 120 sec.; calc.: %; temp.: 105° C.). Approximately 300 mg cell debris was placed on 500 mg pumice granules.

1.8.2 HPLC-MS Conditions for Procedure A

20 µl sample was injected into the HPLC-MS system consisting of a PE Series 200 HPLC provided with a Vydac C4 column (cat.#214TP51) kept at 40° C. coupled to a PE-SCIEX API150EX Mass Spectrometer (MS) with an TurbolonSpray Inlet (L=2, H=7; drying gas flow: 8 l/min and temperature 300° C.). The analytes were eluted using the pump settings shown below (Table 1).

TABLE 1

| HPLC-MS pump settings | | | |
|---|---|---|---|
| Time [min] | Flow [ml/min] | A [%] | B [%] |
| 0 | 0.050 | 100 | 0 |
| 5 | 0.050 | 100 | 0 |
| 15 | 0.050 | 60 | 40 |
| 45 | 0.050 | 0 | 100 |
| 55 | 0.050 | 0 | 100 |
| 57 | 0.050 | 100 | 0 |
| 61 | 0.050 | 100 | 0 |

Mobile phase A: 0.01% (v/v) trifluoroacetic acid + 0.1% (v/v) acetic acid in Milli-Q-Water.
Mobile phase B: 0.008% (v/v) trifluoroacetic acid + 0.1% (v/v) acetic acid in acetonitrile.

The MS signal was obtained in positive mode using different conditions in two mass ranges:
low mass range m/z=450-650: step size was 0.250 amu, dwell time 5 ms, OR=200, RNG=400
high mass range m/z=1000-1800: the step size was 1 amu, dwell time 5 ms, OR=50, RNG=200

1.8.3 HPLC-MS Conditions for Procedure B

The HPLC-MS conditions for procedure B were as described for procedure A except for the following changes with respect to the data collections:
low mass range m/z=450-650: step size was 0.500 amu, dwell time 5 ms, pause time 5 ms
specific haemin mass m/z=616.3 m/z: the step size was 0 amu, dwell time 2000 ms, pause time 5 ms

2. Results

2.1 Results of the Enzymatic Analysis

The specific NADH oxidase and lactate dehydrogenase activities of pellet-frozen cells harvested from each of the four fermentations are listed in Table 2. No NADH oxidase activity was detected in cells from the two anaerobic fermentations A and B. Under aerobic conditions (fermentations C and D), the specific NADH oxidase activity is lowered by 25-30% by the addition of haemin to the fermentation medium. Likewise, addition of haemin lowers the specific lactate dehydrogenase activity by 15-20% under aerobic conditions.

TABLE 2

Enzymatic activities of the cells from the four fermentations [U/mg protein].

|  | Fermentation A | Fermentation B | Fermentation C | Fermentation D |
|---|---|---|---|---|
| NADH oxidase | <0.01 | <0.01 | 0.59 | 0.43 |
| Lactate dehydrogenase | 19.4 | 18.4 | 11.2 | 9.3 |

2.2 Results for Oxygen Content Reducing Effect

The specific oxygen reducing effect of a sample of cells taken during each of the four fermentations is shown in Table 3. As shown in Table 3, the cells which had been grown aerobically in the presence of haemin (fermentation D) were capable of lowering the oxygen content of the milk to a higher extent than cells taken from any of the three other fermentations.

TABLE 3

Oxygen content reducing effect of the cells from the four fermentations

|  | Fermentation A | Fermentation B | Fermentation C | Fermentation D |
|---|---|---|---|---|
| Optical density | 13.2 | 13.9 | 12.8 | 13.3 |
| Inoculation level [%-(w/w)] | 0.091 | 0.086 | 0.094 | 0.090 |
| Dissolved oxygen after 2 hours [mg/kg] | 4.9 | 4.7 | 3.6 | 2.6 |
| Oxygen removed [% of initial amount] | 41 | 43 | 57 | 69 |

2.3 Results of Detection of Porphyrins—Procedure A

Figure 1A:
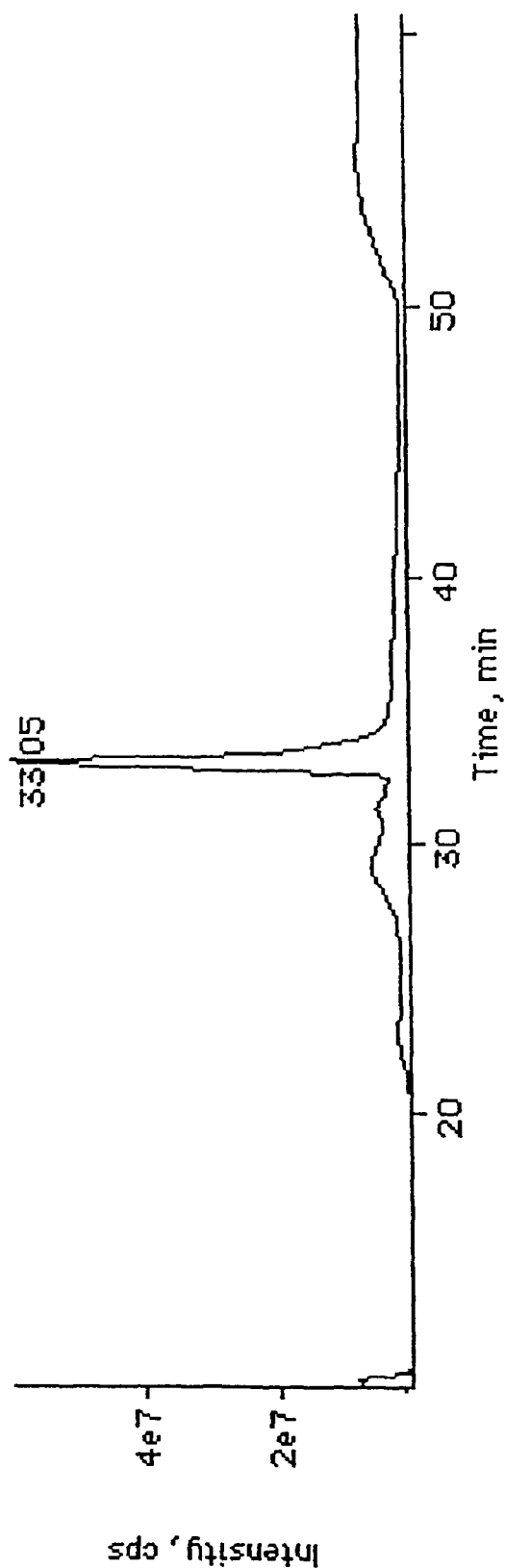
FIG. 1b shows the spectrum of the haemin peak after 33.3 min. The molecular ion of haemin is seen at m/z 616.3 (m/z=mass/charge; cps=counts per second)
Figure 1B:
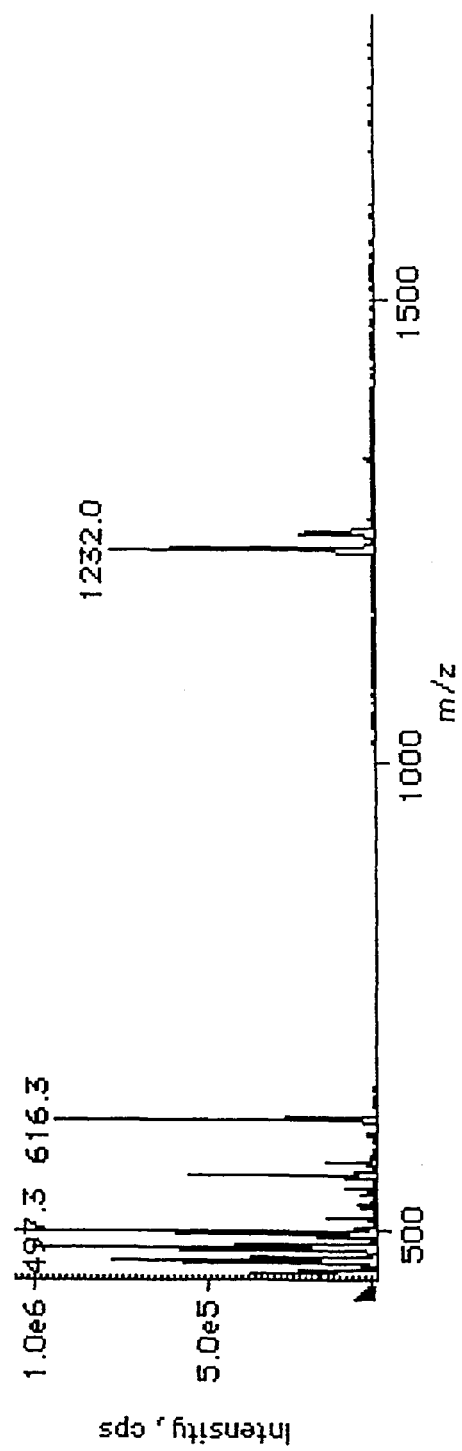
Figure 2A:
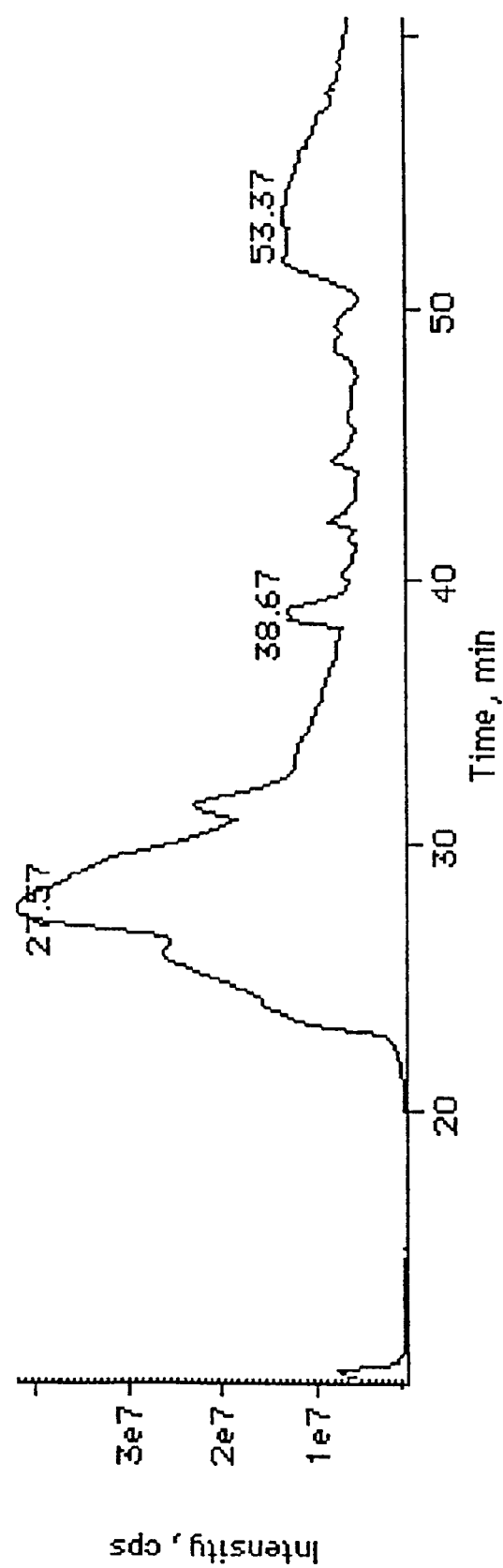
FIG. 2a shows the chromatogram of the cell debris sample of fermentation A of the below Experiment 1.
Figure 2B:
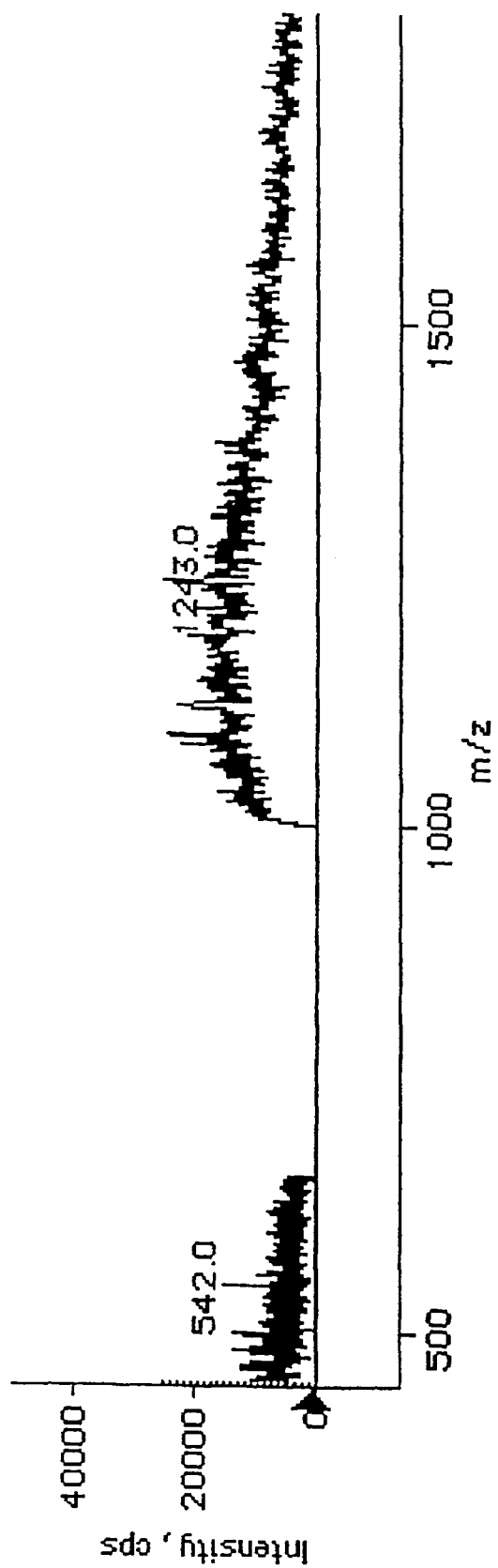
FIG. 2b shows the spectrum of the peak at time 33.3 min in FIG. 2a. The molecular ion of haemin is not seen at m/z 616.3.
Figure 3A:
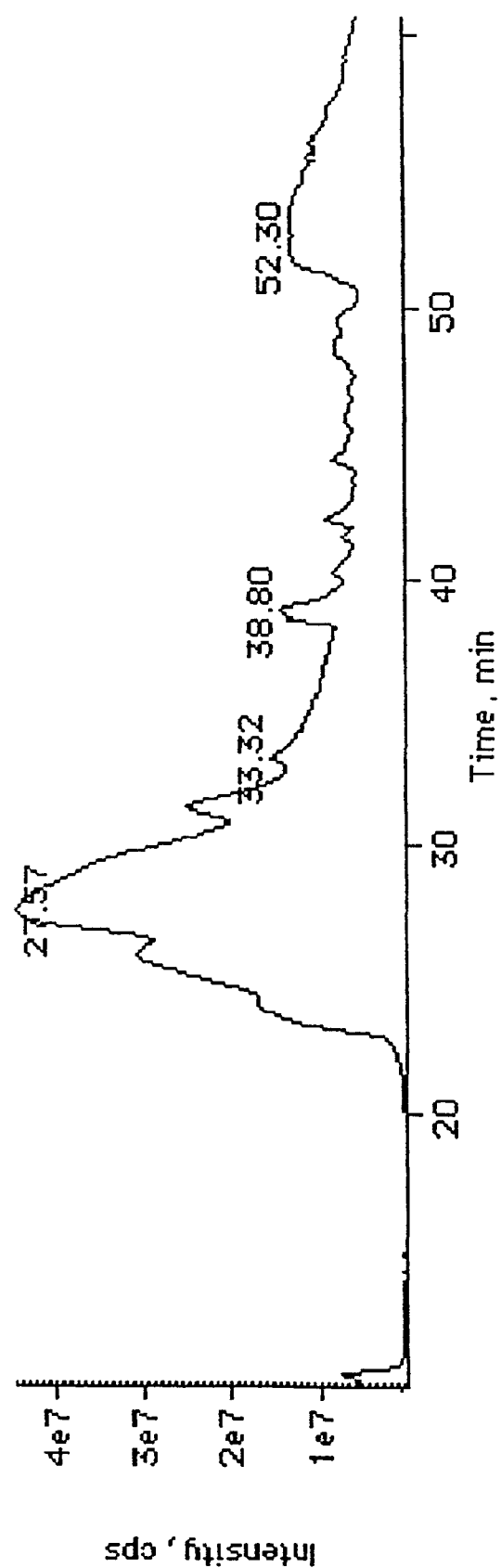
FIG. 3a shows the chromatogram of the cell debris sample of fermentation B of the below Experiment 1.
Figure 3B:
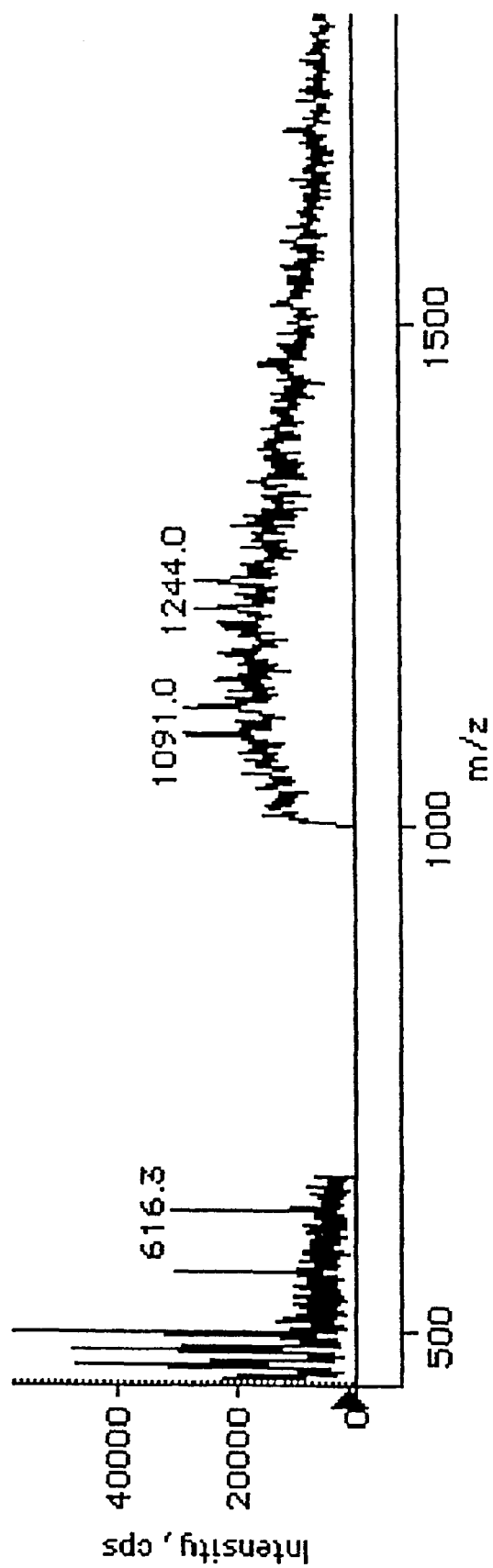
FIG. 3b shows the spectrum of the peak at time 33.3 min in FIG. 3a. The molecular ion of haemin is seen at m/z 616.3.
Figure 4A:
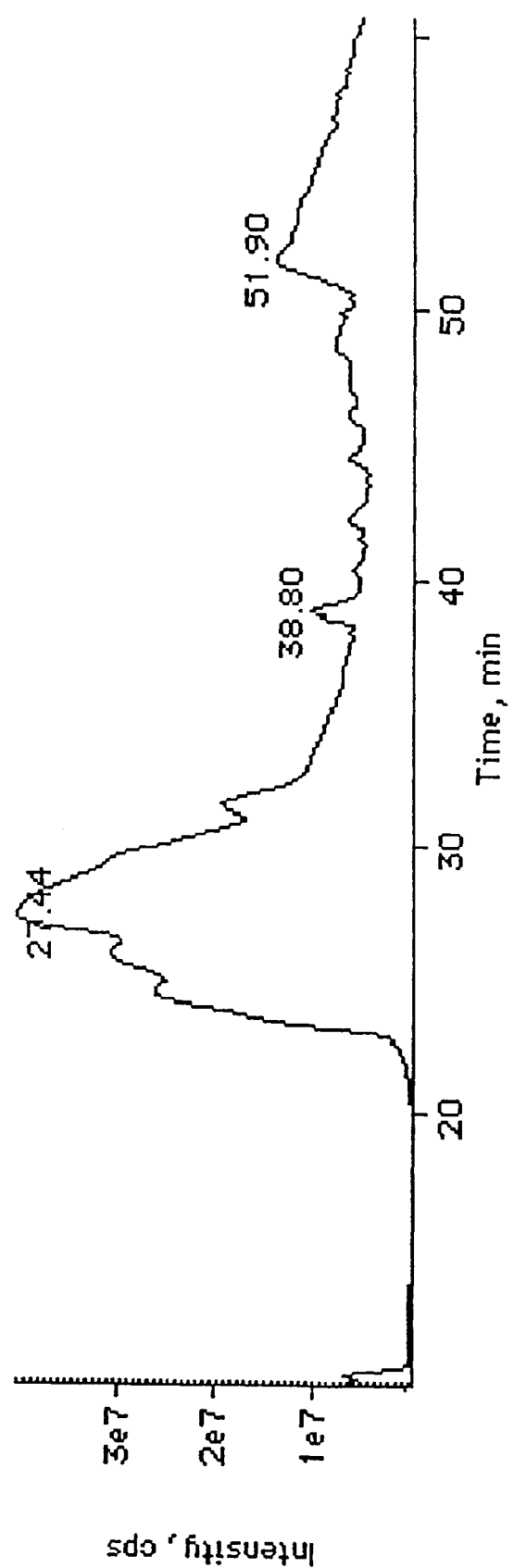
FIG. 4a shows the chromatogram of the cell debris sample of fermentation C of Experiment 1.
Figure 4B:
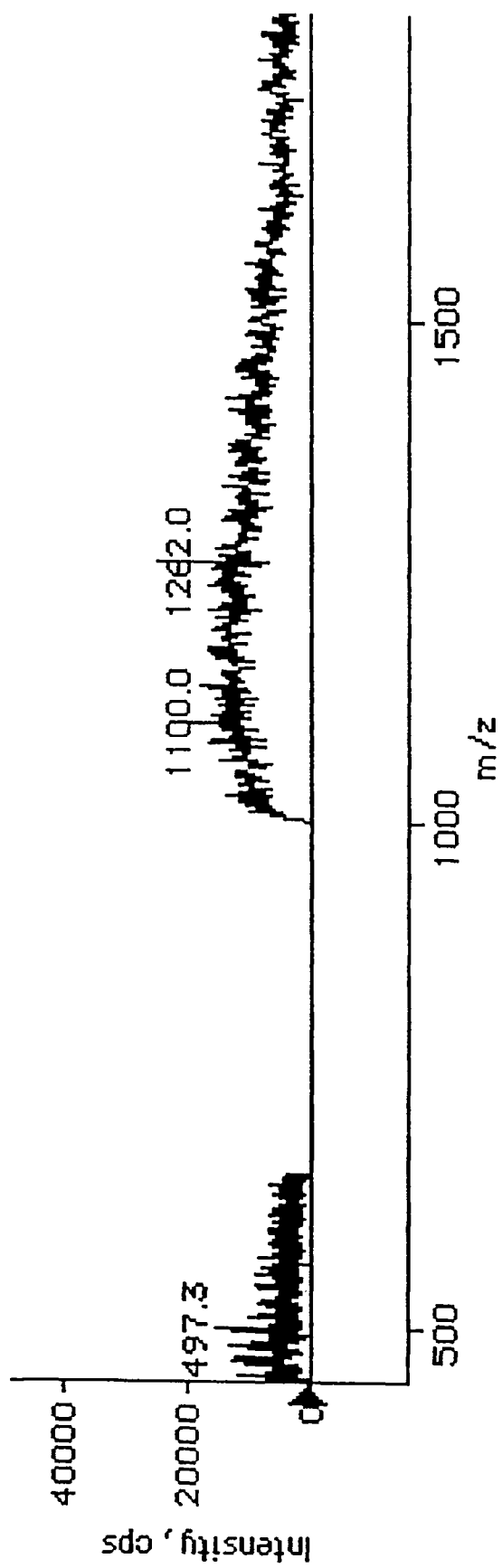
FIG. 4b shows the spectrum of the peak at time 33.3 min in FIG. 4a. The molecular ion of haemin is not seen at m/z 616.3.
Figure 5A:
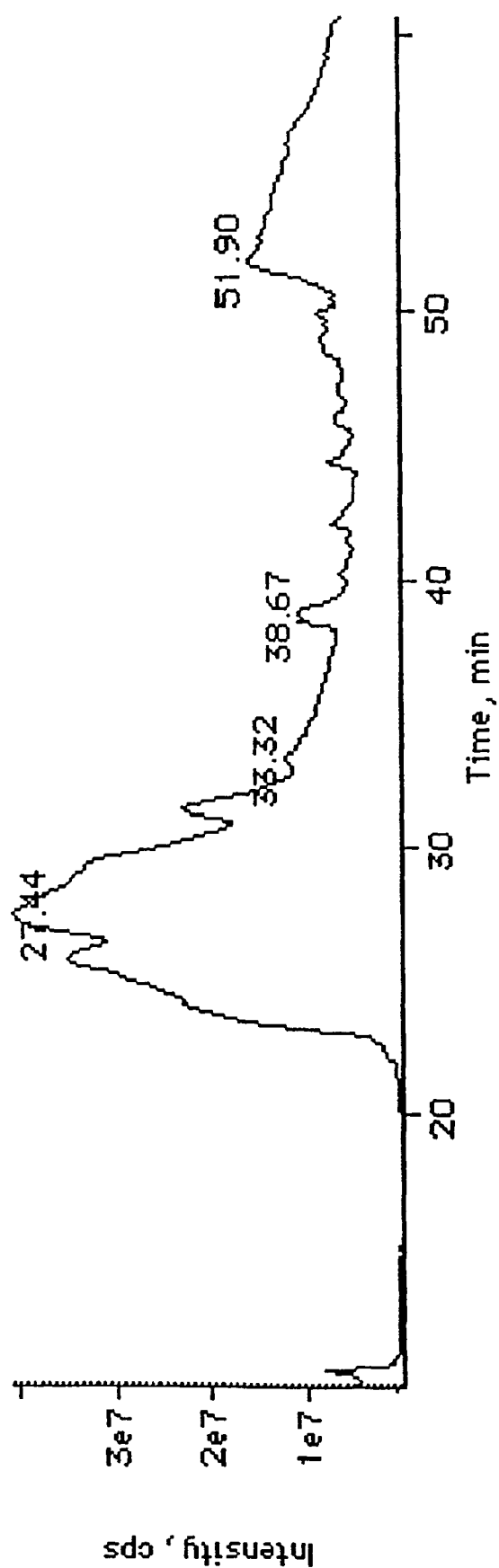
FIG. 5a shows the chromatogram of the cell debris sample of fermentation D of Experiment 1.
Figure 5B:
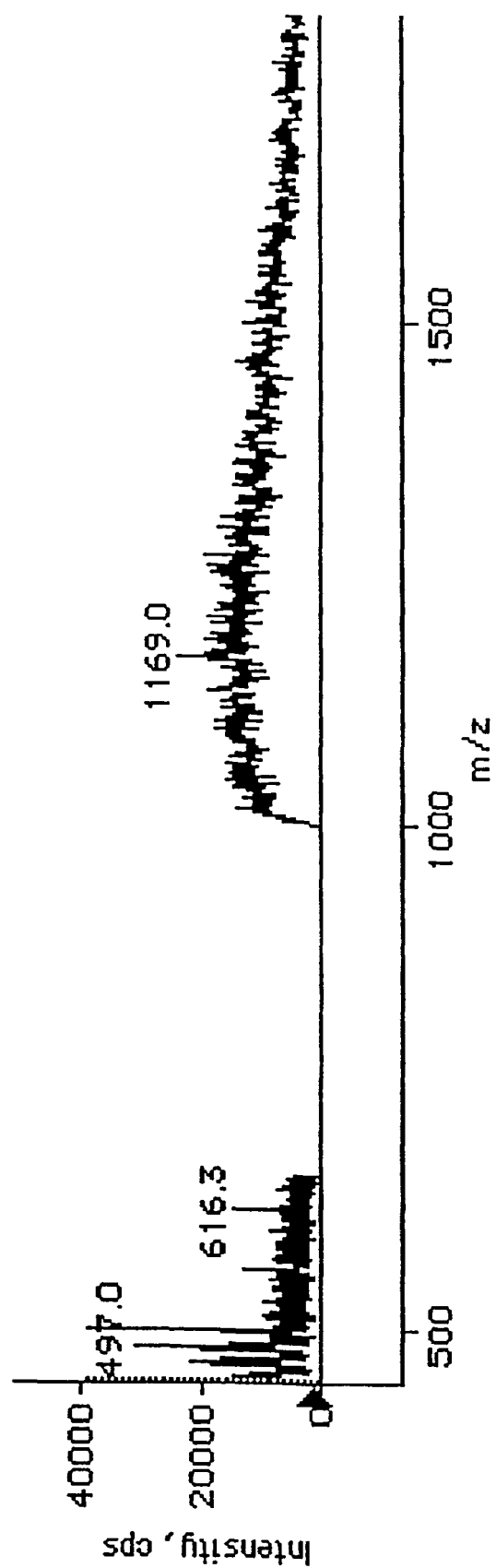
FIG. 5b shows the spectrum of the peak at time 33.3 min in FIG. 5a. The molecular ion of haemin is seen at m/z 616.3.

Using the HPLC-MS method described above, haemin is eluting at a retention time of 33.3 min and is detected as the molecular ion at m/z 616.3 (FIGS. 1a and 1b). No haemin was detected in any of the cell-free extracts from the four fermentations, whereas haemin was detected in the cell pellets (cell debris) when haemin had been present in the fermentation medium (FIGS. 3a, 3b, 5a, and 5b). No haemin was detected in cell pellets (cell debris) from fermentations performed in the absence of haemin (FIGS. 2a, 2b, 4a and 4b).

2.4 Results for Detection of Cytochromes

Using the HPLC-MS method described above, cytochrome c is eluting at a retention time of 23.4 min (FIGS. 6a and 6b) and is detected as the multiply charged intact protein (m/z 1031; 1124; 1237; 1374; 1546; 1766) as well as the ironporphyrin IX ion at m/z 617.3. The method can be applied for detection of other cytochromes than cytochrome c.

2.5 Quantification of Porphyrins—Procedure B

Using purified haemin as standard, the cellular content of haemin was quantified for each of the fermentation A, B, C and D by HPLC-MS using standard addition (Table 4). The dry-matter content of cell debris was quantified to 18.5% (w/w).

As described above, no haemin was detected in cells harvested from fermentations performed on a medium not supplemented with haemin (fermentations A and C), whereas 41 ppm (on a dry weight basis) of haemin was detected in cells from fermentations performed on a medium supplemented with haemin (fermentations B and D).

TABLE 4

Quantification of cellular haemin

|  | Fermentation A | Fermentation B | Fermentation C | Fermentation D |
|---|---|---|---|---|
| Haemin in wet cell debris [ppm] | 0 | 7.6 | 0 | 7.6 |
| Haemin in dry cell debris [ppm] | 0 | 41 | 0 | 41 |

EXPERIMENT 2

1. Materials and Methods 1.1 Microorganisms

A mixed strain starter culture of *Lactococcus lactis* strains was applied in this experiment.

1.2 Medium Composition

Fermentation E was likewise performed using a conventional complex fermentation medium containing lactose as the carbon source. Haemin was added to a final concentration of 10 mg/l.

1.3 Fermentation Conditions

The fermentation was inoculated with a concentrated cell suspension of the *Lactococcus lactis* culture. Air was sparged through the fermentation broth at a rate sufficient to maintain the dissolved oxygen concentration above 50% of saturation level. The fermentation was run at a temperature of 30° C. The culture was allowed to acidify to pH 6.2, whereafter pH was maintained at 6.2 by controlled addition of 13.4 N NH4OH.

1.4 Downstream Processing

The downstream processing was as described in Experiment 1.

1.4.1 Determination of Dry-Matter Content of Frozen Pellets

About 5 g of frozen pellets were weighed into a metal tray positioned on a Sartorius MA 30 balance equipped with a heating device and heated at 160° C. until constant weight. From the loss of weight of the sample, the dry-matter content was calculated.

1.5 Sample Preparation

About 20 g of frozen pellets from fermentation E was weighed out accurately. These pellets were washed twice in cold 20 mM sodium morpholinic propane sulfonic acid (MOPS) buffer (pH 7.4). Following each step of washing, the suspension was centrifuged at 4° C. on a Sorvall RC 50 Plus centrifuge with SS-34 rotor (following first wash: 5,000 rpm for 20 min.; following second wash: 8,000 rpm for 30 min.).

Following the second wash, the cells were resuspended in 10 ml cold MOPS buffer (20 mM, pH 7.4) containing 0.5 mM phenylmethylsulfonylflouride and 5 mM MgSO4 as described in Winstedt et al. (2000). The suspension was then passed through a French Press five times and subsequently centrifuged on the Sorvall centrifuge (4° C., 4,000 rpm, 30 min.). The supernatant was separated and stored at −20° C. until further analysis.

1.6 Spectrophotometric Detection and Quantification of Cytochromes

Prior to analysis, the frozen supernatant was thawed on ice and centrifuged on the Sorvall centrifuge (4° C., 4,000 rpm, 30 min.).

1.5 ml plastic cuvettes were used. 1 ml supernatant was used for both cuvettes. When stated, cyanide was added as 10 μl 0.5 M KCN resulting in a concentration of 5 mM. Also when stated, sodium dithionite was added directly in dry form to cuvettes for reducing the samples.

A Shimadzu UVPC 2101 spectrophotometer was applied (1 nm step; 5 nm slit; "very slow" speed).

1.6.1 CN-Ox and CN/Red-CN Spectra

Untreated sample (=oxidised) was entered into the reference cuvette as well as into the measurement cuvette. Identity of the samples in the two cuvettes was ensured (Ox-Ox spectrum). KCN was added to the measurement cuvette, and the spectrum was recorded (CN-Ox spectrum). Subsequently, KCN was added to the reference cuvette and identity of the samples in the two cuvettes was ensured (CN—CN spectrum). Finally, sodium dithionite was added to the measurement cuvette and the spectrum was recorded after 5-10 min. (CN/Red-CN spectrum).

1.6.2 Red-Ox Spectrum

Untreated sample (=oxidised) was entered into the reference cuvette as well as into the measurement cuvette. Identity of the samples in the two cuvettes was ensured (Ox-Ox spectrum). Then, sodium dithionite was added to the measurement cuvette and the spectrum was recorded after 5-10 min. (Red-Ox spectrum).

1.6.3 Treatment of Spectra

The recorded difference spectra were subjected to minor transformations prior to further data analysis. A straight line was subtracted from the spectra in order to obtain a spectrum in the 500 to 700 nm range without too much tilting. The baseline for the peak at 630 nm was calculated from the values at 612 nm and 658 nm.

2. Results

The recorded difference spectra for cells from fermentation E are shown in FIG. 7. The CN-Ox spectrum (thin line) is without any characteristics in the 500 to 700 nm range. The CN/Red-CN spectrum (dashed line) exhibit a peak at 630 nm—a peak that is smaller than the corresponding peak on the Red-Ox spectrum (thick line), i.e. cyanide "protects" the cytochrome from reduction with dithionite. These observations together with the trough at 650 nm is a strong indication that the cytochrome is cytochrome d (Gil et al., 1992).

The height of the 630 nm peak is 0.0008 AU. By applying an extinction coefficient of 18.8 mM-1 cm-1 (Kita et al., 1984), this corresponds to a cytochrome d concentration of 0.04 µM. Assuming a molecular weight of around 100 kDa, the concentration of cytochrome d is 4 mg/l. Since the initial 20 grams of frozen pellets from fermentation E contained 15.7% (w/w) of dry-matter, the cellular cytochrome d concentration is 13 ppm (mg per kg dry-matter).

No cytochromes were detected in frozen pellets from the anaerobic fermentation in the absence of haemin (fermentation A).

References

Gil, A., Kroll, R. G. & Poole, R. K. 1992. The cytochrome composition of the meat spoilage bacterium *Brochothrix thermosphacta*: identification of cytochrome a3- and d-type terminal oxidases under various conditions. Archives of Microbiology 158:226-233.

Kaneko, T., Takahashi, M. & Suzuki, H., 1990, Acetoin fermentation by citrate-positive *Lactococcus lactis* subsp. *lactis* 3022 grown aerobically in the presence of hemin or $Cu^{2+}$, Applied and Environmental Microbiology 56:2644-2649.

Kita, K., Konishi, K. & Anraku, Y. 1984. Terminal oxidases of *Escherichia coli* aerobic respiratory chain. Journal of Biological Chemistry 259:3375-3381.

Ritchey, T. W. & Seeley Jr., H. W., 1976, Distribution of cytochrome-like respiration in Streptococci. Journal of General Microbiology 93:195-203.

Sijpesteijn, A. K., 1970, Induction of cytochrome formation and stimulation of oxidative dissimilation by hemin in *Streptococcus lactic* and *Leuconostoc mesenteroides*. Antonie van Leeuwenhoek 36:335-348.

von Wachenfeldt, C. & Hederstedt, L. 1992. Molecular biology of Bacillus subtilis cytochromes. FEMS Microbiology Letters 100:91-100.

Winstedt, L., Frankenberg, L., Hederstedt, L. & von Wachenfeldt, C. 2000. *Enterococcus faecalis* V583 contains a cytochrome bd-type respiratory oxidase. Journal of Bacteriology 182:3863-3866.

The invention claimed is:

1. A method of increasing the shelf life and/or the quality of an edible product comprising adding to the product an effective amount of a starter culture composition which is a starter culture comprising a culturally modified lactic acid bacterial cell that has, relative to the cell from which it is derived, an increased content of a porphyrin compound which includes iron,
    wherein said porphyrin compound is haemin, heme or cytochrome d,
    wherein the composition is in the form of a frozen, or freeze dried composition,
    wherein the composition contains an amount of viable culturally modified lactic acid bacterial cells which are in the range of $10^{10}$ to $10^{12}$ CFU per g, and
    wherein the bacterial cell is of a bacterial species selected from the group consisting of *Lactococcus* spp., and *Leuconostoc* spp.,
    wherein shelf life is the period of time in which the edible product is acceptable for consumption.

2. A method of preparing a fermented food or feed product comprising adding to a food or feed product starting material an effective amount of a starter culture composition comprising a culturally modified lactic acid bacterial cell that has, relative to the cell from which it is derived, an increased content of a porphyrin compound which includes iron,
    wherein said porphyrin compound is haemin, heme or cytochrome d,
    wherein the composition is in the form of a frozen or freeze dried composition,
    wherein the composition contains an amount of viable culturally modified lactic acid bacterial cells which are in the range of 1010 to $10^{12}$ CFU per g, and
    wherein the bacterial cell is of a bacterial species selected from the group consisting of *Lactococcus* spp., and *Leuconostoc* spp.

3. A method according to claim 2, wherein the starting material for the food product is selected from the group consisting of milk, a vegetable material, a meat product, a fruit juice, a must, a wine, a dough and a batter.

4. A method according to claim 3, wherein the resulting fermented food product is a dairy product including a product selected from the group consisting of cheese and buttermilk.

5. The method of claim 2, wherein the bacterial cell contains at least 0.1 ppm on a dry matter basis of cytochrome d.

6. A method of preparing a fermented food or feed product comprising adding to a food or feed product starting material an effective amount of a starter culture composition comprising a culturally modified lactic acid bacterial cell that contains at least 0.1 ppm on a dry matter basis of cytochrome d,
    wherein the composition is in the form of a frozen or freeze dried composition,
    wherein the composition contains an amount of viable culturally modified lactic acid bacterial cells which are in the range of $10^{10}$ to $10^{12}$ CFU per g, and wherein the bacterial cell is of a bacterial species selected from the group consisting of *Lactococcus* spp., and *Leuconostoc* spp.

7. The method of claim 1, wherein said edible product is cheese.

8. The method of claim 6, wherein said fermented food product is cheese.

* * * * *

UNITED STATES PATENT AND TRADEMARK OFFICE
CERTIFICATE OF CORRECTION

Page 1 of 1

| | |
|---|---|
| PATENT NO. | : 8,486,468 B2 |
| APPLICATION NO. | : 11/979166 |
| DATED | : July 16, 2013 |
| INVENTOR(S) | : Asger et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 372 days.

Signed and Sealed this
Thirtieth Day of December, 2014

Michelle K. Lee
*Deputy Director of the United States Patent and Trademark Office*